United States Patent
Bishop et al.

(10) Patent No.: US 9,339,420 B2
(45) Date of Patent: May 17, 2016

(54) DISPOSABLE ABSORBENT ARTICLE WITH SIDE LYING LEAKAGE IMPROVEMENT

(75) Inventors: David Fleger Bishop, Appleton, WI (US); Brooke Ashley Zimmer, Neenah, WI (US); Angela Ann Johnston, New London, WI (US); Marcille Faye Ruman, Oshkosh, WI (US); Stephen Carl Baumgartner, Neenah, WI (US); Mary Alice Berceau, DePere, WI (US); Joseph Daniel Coenen, Kaukauna, WI (US); Richard Norris Dodge, II, Appleton, WI (US); Adrienne Rae Loyd, Neenah, WI (US); Connie May McMorrow, Menasha, WI (US); Sara Jane Wille Stabelfeldt, Appleton, WI (US); Katherine Carol Wheeler, Menasha, WI (US)

(73) Assignee: Kimberly-Clark WorldWide, Inc., Neenah, WI (US)

( * ) Notice: Subject to any disclaimer, the term of this patent is extended or adjusted under 35 U.S.C. 154(b) by 1074 days.

(21) Appl. No.: 13/166,927

(22) Filed: Jun. 23, 2011

(65) Prior Publication Data
US 2012/0330260 A1     Dec. 27, 2012

(51) Int. Cl.
| A61F 13/15 | (2006.01) |
| A61F 13/20 | (2006.01) |
| A61F 13/494 | (2006.01) |
| A61F 13/535 | (2006.01) |

(52) U.S. Cl.
CPC ........... *A61F 13/4946* (2013.01); *A61F 13/535* (2013.01)

(58) Field of Classification Search
CPC ....... A61F 13/475; A61F 13/51; A61F 13/49; A61F 13/511; A61F 13/53
USPC ......................................................... 604/378
See application file for complete search history.

(56) References Cited

U.S. PATENT DOCUMENTS

| 4,623,342 A | 11/1986 | Ito et al. |
| 4,808,177 A | 2/1989 | Desmarais et al. |
| 4,895,568 A | 1/1990 | Enloe |
| 5,021,051 A | 6/1991 | Hiuke |
| 5,087,255 A | 2/1992 | Sims |
| 5,364,382 A | 11/1994 | Latimer et al. |
| 5,413,570 A | 5/1995 | Enloe |
| 5,458,592 A | 10/1995 | Abuto et al. |
| 5,466,513 A | 11/1995 | Wanek et al. |
| 5,520,674 A | 5/1996 | Lavon et al. |
| 5,582,606 A | 12/1996 | Bruemmer et al. |
| H1630 H | 1/1997 | Roe et al. |
| 5,601,545 A | 2/1997 | Glaug et al. |
| 5,674,213 A | 10/1997 | Sauer |
| 5,676,661 A | 10/1997 | Faulks et al. |
| 5,814,036 A | 9/1998 | Ronnberg et al. |

(Continued)

FOREIGN PATENT DOCUMENTS

| CN | 1711059 A | 12/2005 |
| CN | 201572255 U | 9/2010 |

(Continued)

*Primary Examiner* — Michele M Kidwell
(74) *Attorney, Agent, or Firm* — Kimberly Clark WorldWide, Inc.

(57) ABSTRACT

An absorbent article having improved leakage protection when the wearer of the absorbent article is lying on their side. The absorbent article has a surge layer in liquid communication with a portion of the garment facing region and a portion of a side edge of the absorbent core.

9 Claims, 7 Drawing Sheets

(56) References Cited

U.S. PATENT DOCUMENTS

| | | | |
|---|---|---|---|
| 5,935,118 A | 8/1999 | Gryskiewicz et al. | |
| 6,222,092 B1 | 4/2001 | Hansen et al. | |
| 6,248,097 B1 * | 6/2001 | Beitz et al. | 604/385.27 |
| 6,436,081 B1 | 8/2002 | Wada et al. | |
| 6,503,525 B1 | 1/2003 | Paul et al. | |
| 6,508,797 B1 | 1/2003 | Pozniak et al. | |
| 6,648,869 B1 | 11/2003 | Gillies et al. | |
| 6,890,327 B2 | 5/2005 | Suzuki et al. | |
| 7,189,888 B2 * | 3/2007 | Wang | A61F 13/53747 604/367 |
| 7,258,758 B2 | 8/2007 | Collier et al. | |
| 2004/0199133 A1 | 10/2004 | Underhill et al. | |
| 2005/0101929 A1 | 5/2005 | Waksmundzki et al. | |
| 2006/0069375 A1 * | 3/2006 | Waksmundzki | A61F 13/51474 604/385.201 |
| 2009/0157023 A1 | 6/2009 | Song et al. | |

FOREIGN PATENT DOCUMENTS

| | | |
|---|---|---|
| DE | 195 34 826 A1 | 3/1997 |
| EP | 0 672 774 B1 | 7/1999 |
| EP | 1 106 152 A1 | 6/2001 |
| EP | 0 539 703 B2 | 10/2005 |
| EP | 1 578 332 B1 | 8/2009 |
| JP | 02-152450 A | 6/1990 |

* cited by examiner

DISPOSABLE ABSORBENT ARTICLE WITH SIDE LYING LEAKAGE IMPROVEMENT

BACKGROUND

It is desired that the attributes of personal care absorbent articles include low leakage of liquid waste from the absorbent article and a dry feel to the wearer. However, absorbent articles commonly fail before the total absorbent capacity of the absorbent article is utilized. Most absorbent articles are designed for a sitting or standing position and have a target area in the crotch region of the absorbent article for containment of liquid waste. The target area is typically centered within the absorbent article for a female wearer and phased forward within the absorbent article for a male wearer. The target area of the absorbent article may be flanked by containment flaps to further aid in containing the liquid waste within the target area and within the absorbent article. The crotch region may also form a bucket away from the wearer's body to hold the fluid until it is absorbed by the absorbent article. When a wearer of an absorbent article is in a side lying position, however, the absorbent article often leaks liquid waste at the leg openings, front waist region or back waist region of the absorbent article. Leakage can occur due to a variety of reasons such as saturation of the absorbent core in the target area, an inability of the target area to handle a gush of fluid, and an insufficient rate of fluid uptake by the absorbent core, especially on the second or third liquid surges.

It has been found that urination can occur at rates as high as 15 to 20 milliliters per second and at velocities as high as 280 centimeters per second. Conventional diaper absorbent structures, such as those comprising admixtures of absorbent gelling particles and cellulosic fluffed pulp, may initially uptake fluid at rates of only about 8 milliliters per second or less, depending on the web density and concentration of gelling particles. The initial uptake rates, however, for conventional absorbent articles can deteriorate once they have already received liquid surges into their absorbent cores. The disparity between liquid delivery and uptake rates can result in excessive pooling on the surface of the absorbent core before it is taken up by the absorbent core. When the wearer of the absorbent article is in a side lying position, the excess fluid follows gravity down to the containment flaps of the absorbent article. The containment flaps may be lying down on the bodyside liner of the absorbent article resulting in gaps between the body of the wearer and the containment flaps. The containment flaps lying on the bodyside liner also decreases the area in which the excess fluid can pool when the wearer is in a side lying position. The excess fluid, therefore, leaks from the absorbent article through a gap between the containment flaps and the body of the wearer or through a gap between the waist regions and the body of the wearer.

Children who wet the bed at night ("nocturnal enuresis") tend to have higher leakage rates. The absorbency challenges are significant for night time child absorbent articles as 70% of children lay on their side and when they experience nocturnal enuresis, they generally are releasing a large volume of urine at high velocity within a single insult.

Thus, there is a need for an absorbent article with side lying leakage improvement that is able to create a space where excess fluid can pool, quickly absorb a large amount of liquid waste in the target area and reduce leakage of liquid waste from the absorbent article when the wearer of the absorbent article is in a side lying position.

SUMMARY

In an embodiment, an absorbent article has an absorbent core which has a wearer facing region, a garment facing region, and a first side edge connecting the wearer facing region and the garment facing region. The absorbent article also has a surge layer which has a first portion in liquid communication with a first portion of the garment facing region of the absorbent core, and a second portion in liquid communication with a portion of the first side edge of the absorbent core. The surge layer of the absorbent article may further have a third portion in liquid communication with a first portion of the wearer facing region of the absorbent core. In an embodiment, the absorbent article may have a second surge layer which has a first portion in liquid communication with a second portion of the garment facing region of the absorbent core and a second portion in liquid communication with a portion of a second side edge of the absorbent core. In an embodiment, the second surge layer may further have a third portion in liquid communication with a second portion of the wearer facing region of the absorbent core. In an embodiment, the absorbent article further has a third surge layer, a portion of which is in liquid communication with the wearer facing region of the absorbent core. In an embodiment, the absorbent article may further have a core wrap. In an embodiment, the absorbent article may further have a pair of containment flaps.

In an embodiment, an absorbent article has an absorbent core which has a wearer facing region, a garment facing region, a first longitudinal side edge connecting the wearer facing region and the garment facing region, a target area; and a surge layer which has a first portion in liquid communication with a first portion of the garment facing region of the absorbent core, a second portion in liquid communication with a portion of the first longitudinal side edge, and a third portion in liquid communication with a first portion of the wearer facing region of the absorbent core; wherein the surge layer is positioned along a longitudinal length of the absorbent core to align with the target area of the absorbent core. In an embodiment, the target area is positioned in a crotch region of the absorbent article. In an embodiment, the target area is positioned between a crotch region and a front waist region of the absorbent article.

In an embodiment, an absorbent article has an absorbent core which has a wearer facing region, a garment facing region, a first longitudinal side edge connecting the wearer facing region and the garment facing region, a second longitudinal side edge laterally opposite the first longitudinal side edge and connecting the wearer facing region and the garment facing region, and has a a surge layer which has a first portion in liquid communication with a first portion of the garment facing region of the absorbent core, a second portion in liquid communication with a portion of the first longitudinal side edge of the absorbent core, a third portion in liquid communication with a first portion of the wearer facing region of the absorbent core, and a fourth portion in liquid communication with a portion of the second longitudinal side edge of the absorbent core. In an embodiment, the absorbent article further has a core wrap. In an embodiment, the absorbent article further has a pair of containment flaps.

DETAILED DESCRIPTION

Figure 1:
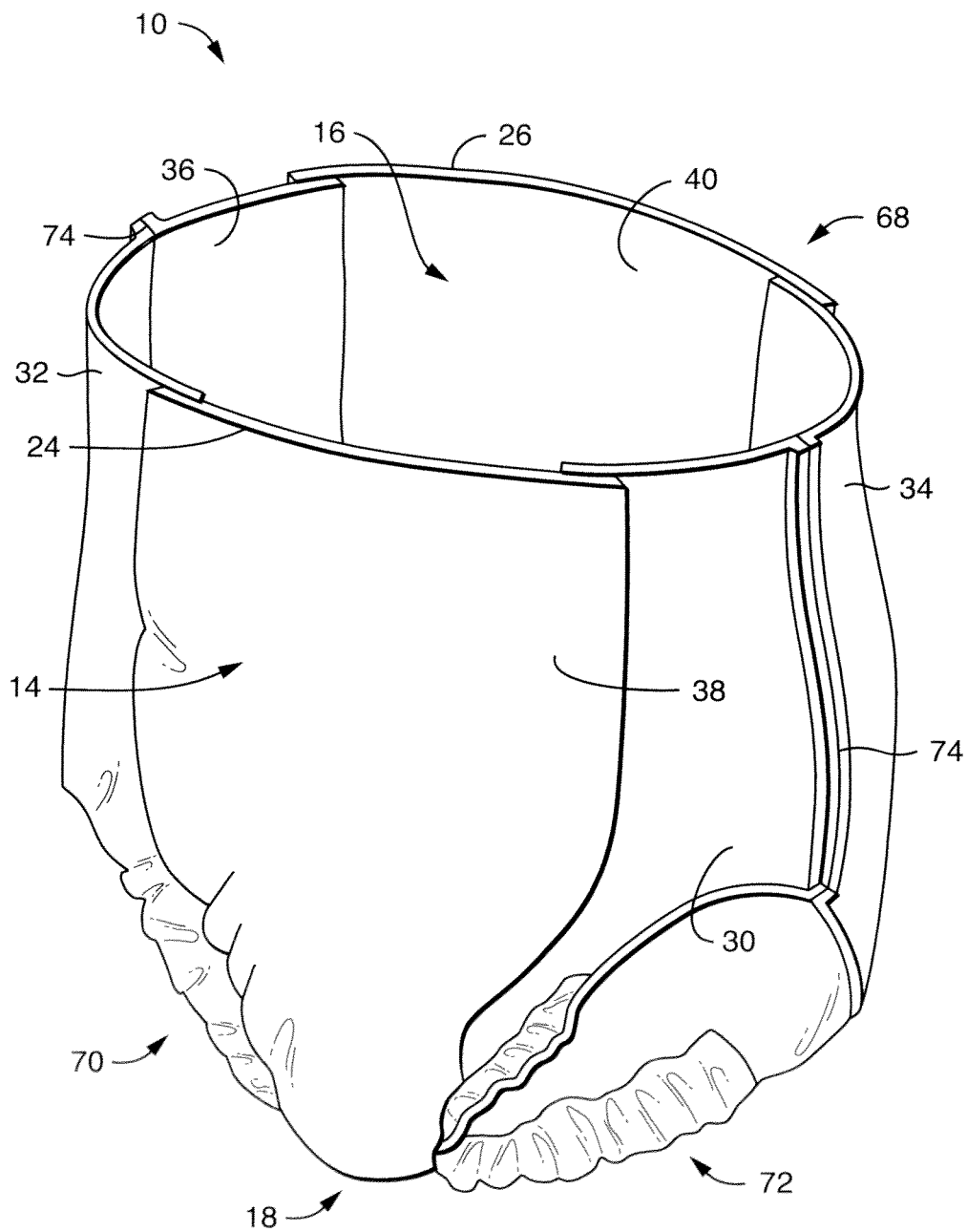
FIG. 1 is a perspective view of an absorbent article.

The present disclosure is generally directed towards an absorbent article having improved leakage protection when the wearer of the absorbent article is lying on their side. As a non-limiting example, the absorbent article has a surge layer in liquid communication with a portion of the garment facing region of the absorbent core and a portion of a side edge such as, for example, a longitudinal side edge, of the absorbent core. In this non-limiting example, the surge layer provides a space for liquid waste to collect while it is absorbed into the absorbent core, such as when the wearer of the absorbent article is in the side lying position.

Definitions:

The term "absorbent article" refers herein to an article which may be placed against or in proximity to the body (i.e., contiguous to the body) of the wearer to absorb and contain various liquid and solid wastes discharged from the body. Such absorbent articles, as described herein, are intended to be discarded after a limited period of use instead of being laundered or otherwise restored for reuse. It is to be understood that the present disclosure is applicable to various disposable absorbent articles including, but not limited to, diapers, training pants, youth pants, swim pants, feminine hygiene products, incontinence products, medical garments, surgical pads and bandages, other personal care or health care garments, and the like without departing from the scope of the present disclosure.

The term "bonded" refers herein to the joining, adhering, connecting, attaching, or the like, of two elements. Two elements will be considered bonded together when they are bonded directly to one another or indirectly to one another, such as when each is directly bonded to intermediate elements.

The term "film" refers herein to a thermoplastic film made using an extrusion and/or foaming process, such as a cast film or blown film extrusion process. The term includes aperture films, slit films, and other porous films which constitute liquid transfer films, as well as films which do not transfer liquid.

The term "g/cc" refers herein to grams per cubic centimeter.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which the liquid body waste, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. which is incorporated herein by reference. Meltblown fibers are microfibers which may be continuous or discontinuous, are generally smaller than about 0.6 denier, and are generally self-bonding when deposited onto a collecting surface. Meltblown fibers used in the present disclosure may be continuous in length.

The term "non-woven" refers herein to materials and webs of material which are formed without the aid of a textile weaving or knitting process.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6 and about 10.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "surge layer" refers herein to a layer capable of rapidly accepting and temporarily holding liquid body waste to decelerate and diffuse a surge or gush of liquid body waste and to subsequently slowly release the liquid body waste therefrom into another layer or layers of the absorbent article.

The term "thermoplastic" refers herein to a material which softens when exposed to heat and which substantially returns to a non-softened condition when cooled to room temperature.

The term "three-dimensional" refers herein to an absorbent article similar to underwear, shorts or pants in that it has continuous leg and waist openings that are bounded by material of which the garment is made. The absorbent article may or may not have manually tearable seams.

Absorbent Article:

Referring to FIG. 1, a disposable absorbent article 10 of the present disclosure is exemplified in the form of a wearer's toilet training pant. By way of illustration only, various materials and methods for constructing an absorbent article 10 such as training pants are disclosed in PCT Patent Application WO 00/37009 published Jun. 29, 2000 by A. Fletcher et al.; U.S. Pat. No. 4,940,464 issued Jul. 10, 1990 to VanGompel et al.; and U.S. Pat. No. 5,766,389 issued Jun. 16, 1998 to Brandon et al., which are incorporated herein by reference. While the embodiments and illustrations described herein may generally apply to absorbent articles manufactured in the machine-direction, it should be noted that one of ordinary skill could apply the information herein to absorbent articles manufactured in the cross-direction without departing from the spirit and scope of the disclosure. The absorbent article 10 includes a front waist region 14, a back waist region 16, and a crotch region 18 interconnecting the front and back waist regions, 14 and 16, respectively. The absorbent article 10 has a pair of laterally opposite side edges, 20 and 22 (shown in FIG. 2), and a pair of longitudinally opposite waist edges, respectively designated front waist edge 24 and back waist edge 26. The front waist region 14 is contiguous with the front waist edge 24 and the back waist region 16 is contiguous with the back waist edge 26.

Figure 2:
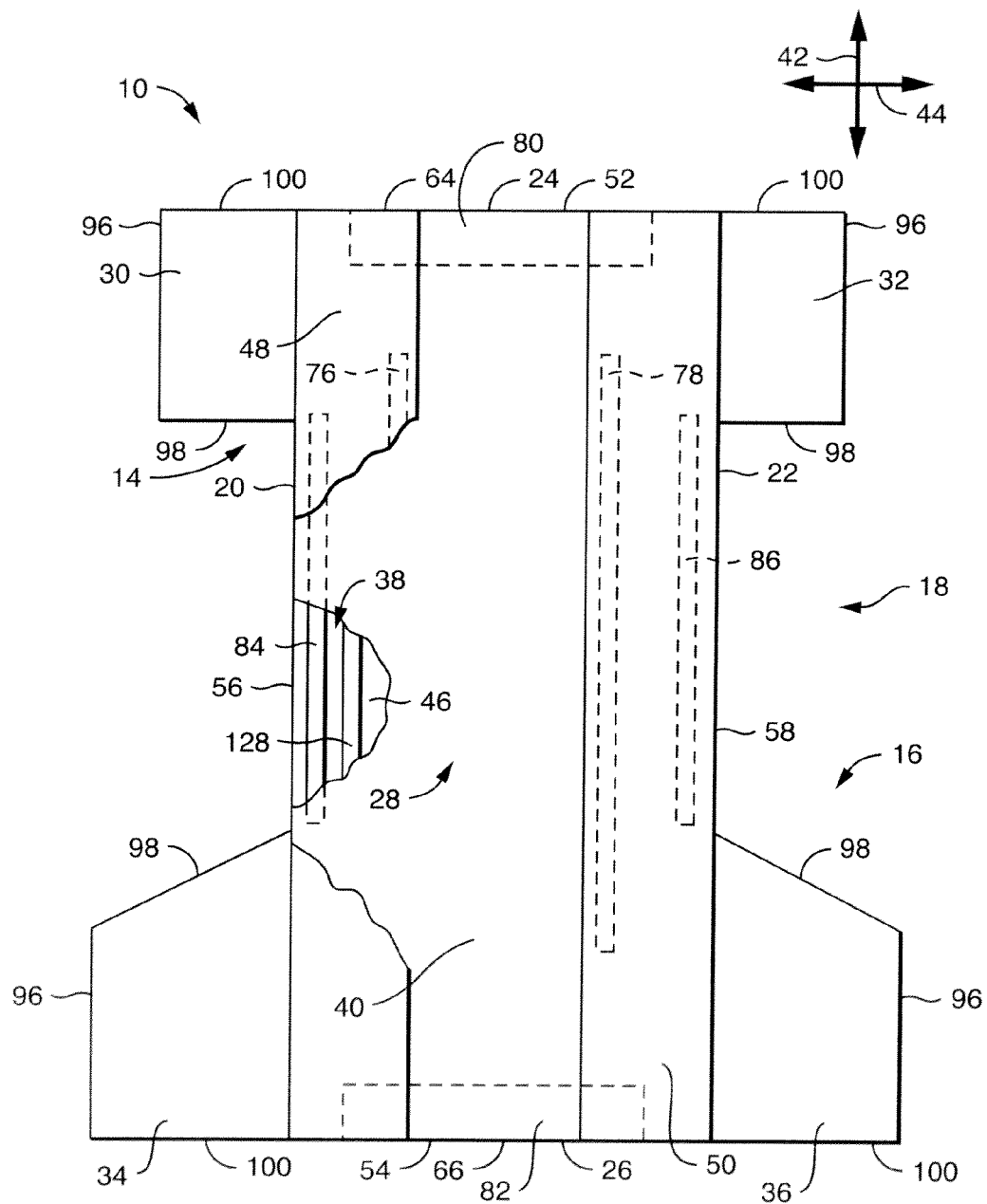
FIG. 2 is a plan view of the absorbent article of FIG. 1 in a stretched and laid flat condition with the bodyside liner facing the viewer and with portions of the absorbent article partially cut away to reveal the underlying features.

Referring to FIG. 2, the absorbent article 10 is illustrated in a stretched and laid flat configuration. The illustrated absorbent article 10 includes a central absorbent assembly 28 which can be rectangular or any other desired shape. The central absorbent assembly 28 includes an outer cover 38 and a bodyside liner 40 bonded to the outer cover 38 in a superposed relation by suitable means such as, but not limited to, adhesives, ultrasonic bonds, thermal bonds, or other conventional techniques. The outer cover 38 defines a length, or longitudinal direction 42, and a width, or lateral direction 44, which, in the illustrated embodiment, coincide with the length and width of the absorbent article 10. An absorbent core 46 is disposed between the outer cover 38 and the bodyside liner 40. A pair of containment flaps, 48 and 50, is secured to the bodyside liner 40 for inhibiting the lateral flow of body wastes. The central absorbent assembly 28 has opposite end edges, 52 and 54, that form portions of the front and back waist edges, 24 and 26, respectively, and opposite side edges, 56 and 58, that form portions of the side edges, 20 and 22, respectively, of the absorbent article 10. The absorbent core 46 comprises longitudinal side edges, 60 and 62 (shown in FIGS. 3-7), which may form portions of the side edges, 56 and 58, of the central absorbent assembly 28 and comprises end edges, 64 and 66, which may form portions of the opposite end edges, 52 and 54, of the central absorbent assembly 28. The absorbent core 46, therefore, may have a length and width that is the same as or less than the length and width of the central absorbent assembly 28.

A pair of laterally opposite front side panels, 30 and 32, extend outward from the central absorbent assembly 28 at the front waist region 14 (thereby forming transversely outer portions of the front waist region 14, and more broadly in part forming transversely opposite sides of the training pant). Laterally opposite back side panels, 34 and 36, extend outward from the central absorbent assembly 28 at the back waist region 16 (thereby forming transversely outer portions of the back waist region 16, and together with the front side panels, 30 and 32, further defining the sides of the training pant).

To form a three-dimensional absorbent article such as a training pant, corresponding front and rear side panels, for example 30 and 34 (e.g., the front left side panel and the rear left side panel) are fastenably secured together using any suitable means such as, but not limited to, adhesives, ultrasonic bonds, thermal bonds, hook and loop, or other conventional techniques. The side panels may be refastenably secured together, or they may be permanently secured together, or they may be formed integrally with each other and with the central absorbent assembly 28. Securing the side panels together provides a central waist opening 68 and a pair of laterally spaced leg openings, 70 and 72.

The front waist region 14 includes the portion of the absorbent article 10 that, when worn, is positioned at least in part on the front of the wearer while the back waist region 16 includes the portion of the absorbent article 10 that, when worn, is positioned at least in part on the back of the wearer. The crotch region 18 of the absorbent article 10 includes the portion of the absorbent article 10 that, when worn, is positioned between the legs of the wearer and covers the lower torso of the wearer. The front side panels, 30 and 32, and the back side panels, 34 and 36, include the portions of the absorbent article 10 (and more particularly of the front and back waist regions, 14 and 16, respectively) that, when worn, are positioned on the hips of the wearer. The secured side panels thus broadly define the transversely opposite sides of the absorbent article 10 at an engagement seam 74. The waist edges, 24 and 26, of the absorbent article 10 are configured to encircle the waist of the wearer and together define the central waist opening 68. Portions of the central absorbent assembly 28 side edges, 56 and 58, in the crotch region 18 generally define the leg openings 70 and 72.

The absorbent article 10 formed into a three-dimensional absorbent article, such as a training pant, is worn by inserting the wearer's feet through the central waist opening 68 and the respective leg openings 70 and 72, grasping the absorbent article 10 near the central waist opening 68 and then pulling the absorbent article 10 up along the wearer's legs until the crotch region 18 of the absorbent article 10 fits snugly against the crotch of the wearer.

The central absorbent assembly 28 is configured to contain and/or absorb liquid and solid wastes discharged from the wearer. For example, the containment flaps 48 and 50 are configured to provide a barrier to the lateral flow of body exudates. A flap elastic member 76 and 78 can be operatively joined to each containment flap 48 and 50 in any suitable manner known in the art. The elasticized containment flaps 48 and 50 define a partially unattached edge that assumes an upright configuration in at least the crotch region 18 of the absorbent article 10 to form a seal against the wearer's body. The containment flaps 48 and 50 can be located along the central absorbent assembly 28 side edges 56 and 58 and can extend longitudinally along the entire length of the central absorbent assembly 28 or can extend partially along the length of the central absorbent assembly 28. Suitable construction and arrangements for containment flaps 48 and 50 are generally well known to those skilled in the art and are described in U.S. Patent No. 4,704,116 issued November 3, 1987 to Enloe, which is incorporated herein by reference.

To further enhance containment and/or absorption of body exudates, the absorbent article 10 suitably includes a front waist elastic member 80, a rear waist elastic member 82 and leg elastic members 84 and 86, as are known to those skilled in the art. The waist elastic members 80 and 82 can be attached to the outer cover 38 and/or the bodyside liner 40 along the opposite central absorbent assembly 28 end edges 52 and 54, and can extend over part or all of the central absorbent assembly 28 end edges 52 and 54. The leg elastic members 84 and 86 can be attached to the outer cover 38 and/or the bodyside liner 40 along the opposite central absorbent assembly 28 side edges 56 and 58 and positioned in the crotch region 18 of the absorbent article 10.

Additional details regarding each of the elements of the absorbent article 10 described herein may be found below and with reference to FIGS. 1-7.

Outer Cover:

The outer cover 38 can be elastic, stretchable or non-stretchable and may be a multi-layer laminate structure of which at least one of the layers is liquid impermeable. In an embodiment, the outer cover 38 can be suitably stretchable and more suitably elastic in at least the lateral or circumferential direction of the absorbent article 10. In another embodiment, the outer cover 38 can be stretchable, and more suitably elastic, in both the lateral and the longitudinal directions. In an embodiment, the outer cover 38 may be a two layer construction, including an outer layer 88 constructed of a liquid permeable material and an inner layer 90 constructed of liquid impermeable material bonded together by a laminate adhesive 92. Suitable laminate adhesives can be applied continuously or intermittently as beads, a spray, parallel swirls, or the like. It is to be understood that the outer cover 38 may instead be constructed of a single layer of impermeable material without departing from the scope of this disclosure.

The liquid permeable outer layer 88 of the outer cover 38 can be any suitable material and may be one that provides a generally cloth-like texture to the wearer. One example of such material is a 20 gsm spunbond polypropylene non-woven web. The outer layer 88 may also be constructed of the same materials from which the bodyside liner 40 is constructed as described herein. It is to be understood that it is not necessary for the outer layer 88 of the outer cover 38 to be liquid permeable.

The liquid impermeable inner layer 90 of the outer cover 38 can be either vapor permeable (i.e., "breathable") or vapor impermeable. The inner layer 90 may be manufactured from a thin plastic film, although other liquid impermeable materials may also be used. The liquid impermeable inner layer 90 (or the liquid impermeable outer cover 38 where the outer cover 38 is of a single-layer construction) inhibits liquid body waste from leaking out of the absorbent article 10 and wetting articles, such as bed sheets and clothing, as well as the wearer and care giver.

Where the outer cover 38 is of a single layer construction, it can be embossed and/or matte finished to provide a more cloth-like appearance. The outer cover 38 can permit vapors to escape from the absorbent article 10 while preventing liquids from passing through. A suitable liquid impermeable, vapor permeable material is composed of a microporous polymer film or a non-woven material which has been coated or otherwise treated to impart a desired level of liquid impermeability.

Absorbent Core:

The absorbent core 46 is suitably constructed to be generally compressible, pliable, non-irritating to the wearer's skin and capable of absorbing and retaining liquid body waste, such as urine. The absorbent core 46 can be manufactured in a wide variety of sizes and shapes (for example, rectangular, trapezoidal, T-shape, I-shape, hourglass shape, etc.) and from a wide variety of materials. The size and the absorbent capacity of the absorbent core 46 should be compatible with the size of the intended wearer and the liquid loading imparted by the intended use of the absorbent article 10. Additionally, the size and the absorbent capacity of the absorbent core 46 can be varied to accommodate wearers ranging from infants to adults.

The absorbent core 46 may have a length ranging from about 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, or 520 mm The absorbent core 46 may have a crotch width ranging from about 50, 55, 60, 65, or 70 mm to about 75, 80, 85, 90, 95, 100, 105, 110, 115, 120, 125, or 130 mm The width of the absorbent core 46 located within the front waist region 14 and/or the back waist region 16 of the absorbent article 10 may range from about 80, 85, 90, or 95 mm to about 100, 105, 110, 115, 120, 125 or 130 mm In an embodiment, the absorbent article 10 is a diaper having the following ranges of lengths and widths of the absorbent core 46 having an hourglass shape: the length may range from about 200, 210, 220, 225, 240 or 250 mm to about 260, 280, 300, 310, 320, 330, 340, 350, 355, 360, 380, 385, or 390 mm; the width of the absorbent core 46 in the crotch region 18 may range from about 50, 55, or 60 mm to about 65, 70, 75, or 80 mm; the width of the absorbent core 46 in the front waist region 14 and/or the back waist region 16 may range from about 80, 85, 90, or 95 mm to about 100, 105, or 110 mm In an embodiment, the absorbent article 10 may be a training pant or youth pant having the following ranges of lengths and widths of the absorbent core 46 having an hourglass shape: the length may range from about 400, 410, 420, 440 or 450 mm to about 460, 480, 500, 510 or 520 mm; the width of the absorbent core 46 in the crotch region 18 may range from about 50, 55, or 60 mm to about 65, 70, 75, or 80 mm; the width of the absorbent core 46 in the front waist region 14 and/or the back waist region 16 may range from about 80, 85, 90, or 95 mm to about 100, 105, 110, 115, 120, 125, or 130 mm In an embodiment, the absorbent article 10 is an adult incontinence garment having the following ranges of lengths and widths of the absorbent core 46 having a rectangular shape: the length may range from about 400, 410 or 415 to about 425 or 450 mm; the width of the absorbent core 46 in the crotch region 18 may range from about 90, or 95 mm to about 100, 105, or 110 mm It should be noted that the absorbent core 46 of an adult incontinence garment may or may not extend into either or both the front waist region 14 or the back waist region 16 of the absorbent article 10.

The absorbent core 46 has a wearer facing region 45 and a garment facing region 47. Side edges, such as longitudinal side edges, 60 and 62, and such as end edges, 64 and 66, connect the wearer facing region 45 to the garment facing region 47. The absorbent core 46 may be constructed of two layers of materials, or in the alternative, may be constructed of a single layer of materials. In an embodiment, the absorbent core 46 comprises an inner layer 102 suitably composed of hydrophilic fibers and an outer layer 104 suitably composed at least in part of a high absorbency material commonly known as superabsorbent material. In an embodiment, the inner layer 102 of the absorbent core 46 is suitably composed of cellulosic fluff, such as wood pulp fluff, and the outer layer 104 of the absorbent core 46 is suitably composed of superabsorbent hydrogel-forming particles, or a mixture of cellulosic fluff and superabsorbent hydrogel-forming particles. As a result, the inner layer 102 has a lower absorbent capacity per unit weight than the outer layer 104. The inner layer 102 may alternatively be composed of a mixture of hydrophilic fibers and superabsorbent material, as long as the concentration of superabsorbent material present in the inner layer 102 is lower than the concentration of superabsorbent material present in the outer layer 104 so that the inner layer 102 has a lower absorbent capacity per unit weight than the outer layer 104. It is also contemplated that the outer layer 104 may be composed solely of superabsorbent material without departing from the scope of this disclosure.

Various types of wettable, hydrophilic fibers can be used in the absorbent core 46. Examples of suitable fibers include cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers composed of nonwettable thermoplastic polymer, such as polypropylene fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. For example, one suitable type of fiber is a wood pulp that is a bleached, highly absorbent sulfate wood pulp containing primarily soft wood fibers. However, the wood pulp can be exchanged with other hydrophilic fiber materials, such as synthetic, polymeric, or meltblown fibers or with a combination of meltblown and natural fibers.

Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Shapes having a largest greatest dimension/smallest dimension ratio, such as needles, flakes, and fibers are also contemplated for use herein. Conglomerates of particles of superabsorbent materials may also be used in the absorbent core.

The absorbent core 46 overlays the inner layer 90 of the outer cover 38, extending laterally between the leg elastic members, 84 and 86, and is secured to the inner layer 90 of the outer cover 38, such as by being bonded thereto with adhesive. However, it is to be understood that the absorbent core 46 may be unsecured to the outer cover 38 and remain within the scope of this disclosure.

Core Wrap:

The absorbent core 46 may be partially or completely encompassed by a core wrap 162. The core wrap 162 maintains the integrity and/or shape of the absorbent core 46. The core wrap 162 may be well-suited for containing absorbent cores which are made at least partially of particulate material such as superabsorbent material. The core wrap 162 can be composed of a cellulosic material, such as creped material or a high wet-strength tissue, a meltblown web, a spunbond web, a carded web, or a combination thereof. Once the core wrap 162 has been wrapped around the absorbent core 46, the core wrap 162 should not unduly expand or stretch as this might cause particulate material to escape from the absorbent core 46. In an embodiment, the core wrap 162, while in a dry state, should have respective elongation values at peak load in the machine and cross directions of 30 percent or less and 40 percent or less. In an embodiment, the core wrap 162 may have a longitudinal length the same as the longitudinal length of the absorbent core 46.

The core wrap 162 is typically wrapped about the absorbent core 46 over the wearer facing region 45 and the garment facing region 47 as well as the side edges. In an embodiment, the core wrap 162 completely wraps around the absorbent core 46 and is sealed to itself. In an embodiment, the core wrap 162 may be folded over on itself and then sealed using, for example, heat and/or pressure. In an embodiment, the core wrap 162 may be composed of separate sheets of core wrap which are utilized to encapsulate the absorbent core 46 and sealed together using a sealing means such as an ultrasonic bonder or other thermochemical bonding means or the use of an adhesive. Additional details regarding the core wrap 162 may be found in U.S. Pat. No. 5,458,592 issued Oct. 17, 1995 to Abuto et al. which is herein incorporated by reference. It should be noted that it is not necessary that the absorbent core 46 is encompassed by a core wrap 162.

Surge Layer:

A surge layer, such as surge layer 128 (shown in FIG. 3), having an inner surface 130 and an outer surface 132 is positioned between the bodyside liner 40 and the outer cover 38 to help decelerate and diffuse surges or gushes of liquid body waste penetrating the bodyside liner 40. The inner surface 130 of the surge layer 128 faces the absorbent core 46 and the outer surface 132 of the surge layer 128 faces away from the absorbent core 46. A portion of the inner surface 130 of the surge layer 128 is in liquid communication with a portion of at least one of the following: the wearer facing region 45, the garment facing region 47, a side edge, such as longitudinal side edges, 60 and 62, and end edges, 64 and 66, and combinations thereof, of the absorbent core 46.

The absorbent article 10 contains at least one surge layer 128. The absorbent article 10 may contain more than one surge layer. The absorbent article 10 may contain one, two, three, four, five, six, seven, eight, nine, or ten surge layers. In an embodiment in which the absorbent article 10 contains more than one surge layer, it is to be understood that it is not necessary for each surge layer to have the same configuration as any other surge layer within the absorbent article 10. Non-limiting configurations of surge layers are described and illustrated herein. While particular configurations are described and illustrated herein, it is to be understood that additional configurations of surge layers within an absorbent article 10 are possible without departing from the spirit and scope of this disclosure.

In an embodiment in which the absorbent article 10 contains more than one surge layer, the multiple surge layers may be in liquid communication with each other. In such an embodiment, the multiple surge layers may be in liquid communication with each other in a region in which the surge layers overlap, in a region in which the surge layers are contiguous with each other, and combinations thereof. It is to be understood that in an absorbent article 10 having multiple surge layers, the surge layers need not be in liquid communication with each other and, therefore, the surge layers may be configured in the absorbent article 10 to be spaced apart from and not contiguous with each other.

The surge layer(s) may have any longitudinal length dimension as deemed suitable. In an embodiment, the longitudinal length of the surge layer is the same as the longitudinal length of the absorbent core 46. In such an embodiment the midpoint of the longitudinal length of the surge layer substantially aligns with the midpoint of the longitudinal length of the absorbent core 46. In an embodiment, the longitudinal length of the surge layer is shorter than the longitudinal length of the absorbent core 46. In such an embodiment, the surge layer may be positioned to be in liquid communication with the absorbent core 46 at any desired location along the longitudinal length of the absorbent core 46. As an example of such an embodiment, the absorbent core 46 may contain a target area where repeated liquid surges typically occur in the absorbent article 10. The particular location where liquid is discharged varies depending on the age and gender of the wearer. For example, males tend to urinate further toward the front end of the absorbent article 10 and the target area may be phased forward within the absorbent article 10. The female target area is located closer to the center of the crotch region 18 of the absorbent article 10. As a result, the relative longitudinal placement of the surge layer within the absorbent article 10 can be selected to best correspond with the actual target area of either or both categories of wearers. In an embodiment, the absorbent core 46 may contain a target area centered within the crotch region 18 of the absorbent article 10 with the premise that the absorbent article 10 would be worn by a female wearer. The surge layer, therefore, may be positioned along the longitudinal length of the absorbent core 46 such that the surge layer is substantially aligned with the target area of the absorbent article 10 intended for a female wearer. Alternatively, the absorbent article 10 may contain a target area positioned between the crotch region 18 and the front waist region 14 of the absorbent article 10 with the premise that the absorbent article 10 would be worn by a male wearer. The surge layer, therefore, may be positioned along the longitudinal length of the absorbent core 46 such that the surge layer is substantially aligned with the target area of the absorbent article 10 intended for a male wearer.

The surge layer(s) may have a longitudinal length from about 120, 130, 140, 150, 160, 170, 180, 190, 200, 210, 220, 225, 230, 240, or 250 mm to about 260, 270, 280, 290, 300, 310, 320, 340, 350, 360, 380, 400, 410, 415, 420, 425, 440, 450, 460, 480, 500, 510 or 520 mm In an embodiment in which the absorbent article 10 is a diaper, the surge layer may have a longitudinal length from about 120, 130, 140, 150, 160, 170, or 180 mm to about 200, 210, 220, 225, 240, 260, 280, 300, 310 or 320 mm In such an embodiment, the surge layer may be shorter in longitudinal length than the longitudinal length of the absorbent core 46 and may be phased from the front end edge 52 of the absorbent core 46 a distance of from about 15, 20, or 25 mm to about 30, 35 or 40 mm In an embodiment in which the absorbent article 10 may be a training pant or youth pant, the surge layer may have a longitudinal length from about 120, 130, 140, 150, 200, 210, 220, 230, 240 or 250 mm to about 260, 270, 280, 290, 300, 340, 360, 400, 410, 420, 440, 450, 460, 480, 500, 510 or 520 mm In such an embodiment, the surge layer may have a longitudinal length shorter than the longitudinal length of the absorbent core 46 and may be phased a distance of from about 25, 30, 35 or 40 mm to about 45, 50, 55, 60, 65, 70, 75, 80 or 85 mm from the front end edge 52 of the absorbent core 46. In an embodiment in which the absorbent article 10 is an adult incontinence garment, the surge layer may have a longitudinal length from about 200, 210, 220, 230, 240, or 250 mm to about 260, 270, 280, 290, 300, 320, 340, 360, 380, 400, 410, 415, 425, or 450 mm In such an embodiment, the surge layer may have a longitudinal length shorter than the longitudinal length of the absorbent article 10 and the surge layer may be phased a distance of from about 20, 25, 30 or 35 mm to about 40, 45, 50, 55, 60, 65, 70 or 75 mm from the front end edge 52 of the absorbent core 46.

The surge layer(s) may have any total width as desired. The total width of the surge layer is measured with the surge layer in a laid flat configuration. The surge layer may have a total width dimension from about 20, 25, 30, 35, 40, 45, 50, 55, 60, 70, 80, 90 or 100 mm to about 110, 115, 120, 130, 140, 150, 160, 165, 170, 175, 180, 185, 190, 195, 200, 210, 220, 230, 240, 250 or 260 mm As will be understood, the total width of the surge layer may vary dependent upon whether the absorbent article 10 has a single surge layer or multiple surge layers. The total width of the surge layer may also vary dependent upon the size and shape of the absorbent article 10 within which the surge layer will be placed. In an embodiment in which the absorbent article 10 is a diaper, the surge layer may have a total width dimension from about 20, 25, 30, 35, 40, 50, 55, 60 or 70 mm to about 80, 90, 100, 110, 115, 120, 130, 140, 150, 160, 165, 170, 175, 200, 210 or 220 mm. In an embodiment in which the absorbent article 10 may be a training pant or youth pant, the surge layer may have a total width dimension from about 15, 20, 25, 30, 40, 45, 50, 55, 60, 70, 80, 90 or 100 mm to about 110, 115, 120, 130, 140, 150, 160, 165, 170, 175, 180, 185, 190, 195, 200, 210, 220, 230, 240, 250 or 260 mm In an embodiment in which the absorbent article 10 is an adult incontinence garment, the surge layer may have a total width dimension from about 20, 25, 30, 35, 40, 45, 50, 55, 60, 70 or 80 mm to about 90, 100, 110, 115, 120, 130, 140, 150, 160, 165, 170, 175, 180, 190, 200 or 220 mm It should be noted that in an absorbent article 10 having more than one surge layer, the surge layers may each have the same total width, may have different total widths or combinations thereof.

The lateral width of the surge layer(s) is the measure of the portion of the surge layer extending in the lateral direction of the absorbent article 10 and in liquid communication with either the garment facing region 47 or the wearer facing region 45 of the absorbent core 46. The lateral width of a portion of a surge layer in liquid communication with the wearer facing region 45 of the absorbent core 46 may range from about 5, 10, 15, 20, 25, 30, 35, 40, 45, 50, 55 or 60 mm to about 65, 70, 75, 80, 85, 90, 95, 100, 105, 110, 115, 120, 125, or 130 mm In an embodiment in which at least one surge layer is in liquid communication with at least a portion of the garment facing region 47 of the absorbent core 46, it should be noted that the surge layer may be, but is not necessarily, in liquid communication with the entire garment facing region 47 of the absorbent core 46. In an embodiment in which the absorbent article 10 has a single surge layer, the total lateral width of the portions of a single surge layer in liquid communication with two laterally opposite portions of the garment facing region 47 of the absorbent core 46 may range from about 5, 10, 15, 20, 25, 30, 35, 40, 45, or 50 mm to about 55, 60, 65, 70, 75, 80, 85, 90, 95, 100, or 110 mm In an embodiment in which the absorbent article 10 has a single surge layer, the surge layer may be in liquid communication with the garment facing region 47 in a percentage ranging from about 5, 10, 15, 20, 25, 30, 35, or 40% to about 45, 50, 55, 60, 65, 70, 75, 80, 85 or 90%. In an embodiment in which the absorbent article 10 has at least two surge layers in liquid communication with the garment facing region 47 of the absorbent core 46, each portion of each surge layer in liquid communication with the garment facing region of the absorbent core may have a lateral width from about 5, 10, 15, 20, 25 or 30 mm to about 35, 40, 45, 50, or 55 mm In an embodiment in which the absorbent article has more than one surge layer, the combination of surge layers may be in liquid communication with the garment facing region 47 of the absorbent core 46 in an percentage ranging from about 5, 10, 15, 20, 25, 30, 35 or 40% to about 45, 50, 55, 60, 65, 70, 75, 80, 85 or 90%.

It should be understood that the percentage of surge layer in liquid communication with the garment facing region 47 of the absorbent core 46 may be uniform along the longitudinal length of the absorbent core 46 or may vary along the longitudinal length of the absorbent core 46. As noted above, the absorbent core 46 may be manufactured in a wide variety of sizes and shapes such as, for example, rectangular, trapezoidal, T-shape, I-shape, hourglass shape, etc. It should be understood that an absorbent article 10 having a rectangular absorbent core 46 and a surge layer having uniform lateral width may have no variance in the percentage of surge layer in liquid communication with the garment facing region 47 of the absorbent core 46. It should be understood that an absorbent article 10 having an absorbent core 46 with an hourglass shape, for example, and a surge layer having uniform lateral width, may have variance, in the longitudinal direction, in the percentage of surge layer in liquid communication with the absorbent core 46 as the width of the absorbent core 46 may be wider in the front waist region 14 and back waist region16 than in the crotch region 18. In such an embodiment, the lateral width of the surge layer may be uniform through the front waist region 14, back waist region and 16 crotch region 18 but the percentage of surge layer in liquid communication with the garment facing region 47 of the absorbent core 46 may be smaller in the crotch region 18 than in the front and back waist regions 14 and 16. In such an embodiment, the surge layer may be contiguous with the longitudinal side edges, 60 and 62, in the front and back waist regions, 14 and 16, respectively, and may extend beyond the longitudinal side edges, 60 and 62, in the crotch region 18.

When the surge layer is in a laid-flat condition, the surge layer may have a height of equal to or greater than about 1.5, 2, 2.5, 3, 3.5, 4, 4.5, or 5 mm The surge layer may have a generally uniform height and cross-sectional area when in a laid-flat condition. Alternatively, the surge layer may vary in height and cross-sectional area when in a laid-flat condition. The height of the surge layer when in a laid-flat condition may be any desired height and may be selected dependent upon the final configuration of the surge layer in the absorbent article 10 as well as the age and gender of the wearer. In an embodiment, the absorbent core 46 may have a height from about 1, 2 or 3 to about 6, 7, or 8 mm In such an embodiment, the placement of the surge layer in liquid communication with the absorbent core 46 in the manner described herein may result in a total height of the absorbent core 46 and surge layer ranging from about 4 or 5 mm to about 10, 11 or 12 mm The surge layer can rapidly accept and temporarily hold the liquid body waste prior to slowly releasing the liquid body waste for flow toward the absorbent core 46. The surge layer can include various types of woven and non-woven fabrics, such as spunbond fabrics, meltblown fabrics, bonded carded webs, through-air bonded carded webs, knit fabrics, woven fabrics, airformed fabrics and the like, as well as combinations thereof. In an embodiment, the surge layer may be an apertured film. The fabrics can be composed of various types of fibers, such as polyolefin fibers, polyester fibers, bicomponent fibers, conjugate fibers, curly fibers, and the like, as well as combinations thereof. The fibers may be short staple length fibers such as are used in the airlaying, bonding and carding processes, or longer more continuous fibers such as formed in the spunbond process. Typical staple length fiber lengths may range from about 5, 15, 20, 25, 30, 35 to about 40, 45, 50, or 55 millimeters, though lengths outside of this range may also be used. As a non-limiting example, airlaying typically involves using fibers with lengths in the range of about 5 to about 20 millimeters. Fiber diameters typically may range from about 1.5 to about 16 denier, and in another embodiment, from about 3 to about 6 denier. The fibers of the surge layer may be crimped, circular or noncircular including, for example, bilobal, trilobal, and x-shaped cross-sections. The fibers may be solid or hollow. Additionally, the fibers may be made from a single fiber polymer or from multiple polymers such as are commonly found in biconstituent and bi- or multicomponent fibers. When using bicomponent fibers, fiber cross-sections may include, for example, sheath/core, side-by-side and islands-in-the-sea cross sections. The resultant fibrous surge layer may be a uniformly mixed homogeneous single layer blend of the selected type fiber or fibers.

The surge layer may have various parameters including basis weight, void volume, permeability, porosity, surface area per void volume, hydrophilicity, compression resiliency and saturation capacity. In an embodiment, the basis weight of the surge layer is at least about 20 gsm. In an embodiment, the basis weight of the surge layer is from about 20, 30, 40, 50 or 60 gsm to about 70, 80, 90, 100, 110, 120, 130, 140, 150, or 160 gsm. The void volume of the surge layer is a measure of how much air space is in the structure. The void volume is measured at 689 dynes per square centimeter (0.01 pounds per square inch) and may range from about 40, 45, 50, 55 or 60 to about 80, 85, 90, 95, 100, 105, 110, 115, or 120 cubic centimeters per gram of surge layer. The permeability indicates the ability of the surge layer to conduct fluid through it. When a fluid initially enters the surge layer, fluid movement is dominated by forced flow from the momentum of the insult velocity of the fluid. Capillarity may not be significant in this flow regime as it may not have enough time to control the fluid path, thus, fluid flow through the surge layer will be controlled by the permeability of the surge layer on the initial insult. Permeability for the surge layer may range from about 2,000, 4,000, 5,000, 7,000, 8,000 or 9,000 darcies to about 10,000, 11,000, 12,000, 13,000, 14,000, or 15,000 darcies.

The porosity of the surge layer is the ratio of the amount of void space in the surge layer to the total volume of the surge layer. The porosity of the surge layer, as measured at a pressure of 689 dynes per square centimeter (0.01 pounds per square inch), may range from about 95 or 97% to about 98 or 99%. The surface area per void volume, with the void volume being measured at a pressure of 689 dynes per square centimeter (0.01 pounds per square inch), may range from about 10, 15, 20, or 25 to about 30, 30, 45 or 50 square centimeters per cubic centimeter. Permeability is the result of fluid having to travel over and around fiber surfaces when under forced flow in order to occupy the void spaces within the surge layer. Surface area per void volume (SA/VV) indicates how closely together those fiber surfaces are located to each other. Thus, SA/VV can control the amount of permeability for a surge layer. A high SA/VV value indicates there is a large amount of surface area which is placed closely together. Increases in SA/VV can be achieved by using smaller fibers which increases the surface area per unit weight or by making the surge layer more dense which decreases the void volume per unit weight. When SA/VV increases, permeability decreases since fluid is forced to travel over and around more surfaces to get through the surge layer. If the SA/VV becomes too high, then the permeability will be too low to allow easy fluid entry into and flow through the surge layer. In an embodiment, the SA/VV is below about 50 square centimeters per cubic centimeter.

To ensure rapid uptake of fluid, the overall surge layer should have hydrophilic tendencies. It is desirable that at least a portion of the fibers have a contact angle less than 90 degrees. As a result, a surge layer will have sufficiently hydrophilic tendencies when the surge layer has a saturation capacity from about 40, 45, 50, 55, or 60 to about 65, 70, 75, or 80 grams of 0.9% saline solution per gram of surge layer. The surge layer may have compression resilience, in both the wet and dry states, of at least about 60, 65, 70, 75, 80, or 85%. In such an embodiment, the surge layer will be able to absorb a larger volume of fluid upon rapid insult and will not readily collapse once the fluid has been absorbed. A collapse of the surge layer would result in a reduced capacity for retaining the fluid.

Examples of suitable surge layers are described in U.S. Pat. Nos. 5,486,166; 5,490,846; 5,562,650; and 5,364,382, the entire disclosures of which are hereby incorporated by reference in a manner that is consistent herewith.

The bodyside liner 40 may be secured to the surge layer such as by being bonded thereto using a suitable adhesive and to the absorbent core 46, such as by being bonded thereto by additional adhesive. However, it is understood that the bodyside liner 40 may be unsecured to the surge layer and/or to the absorbent core 46 without departing from the scope of this disclosure.

Figure 3:
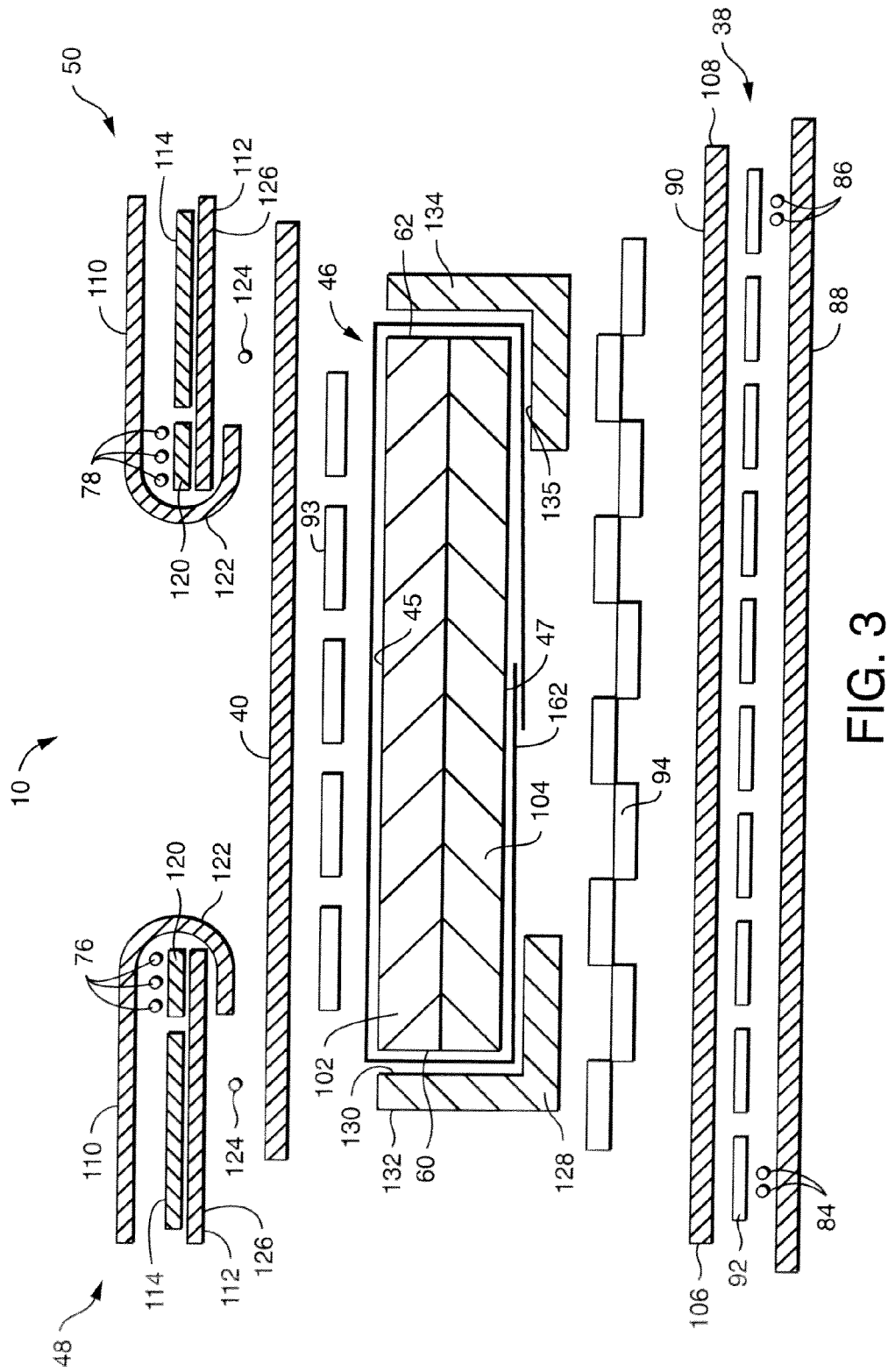
FIG. 3 is a separated cross-section of the absorbent article of FIG. 1 taken laterally through the crotch region of the absorbent article.

FIG. 3 is an illustration of a separated cross-section of an embodiment of an absorbent article 10, such as a training pant, comprising two surge layers 128 and 134. In such an embodiment, a first portion of the inner surface 130 of surge layer 128 and a first portion of the inner surface 135 of surge layer 134 are in liquid communication with first and second portions, respectively, of the garment facing region 47 of the absorbent core 46. Also in such an embodiment, a second portion of the inner surface 130 of surge layer 128 and a second portion of the inner surface 135 of surge layer 134 are in liquid communication with portions of the longitudinal side edges, 60 and 62, respectively, of the absorbent core 46. It is to be understood that in the illustrated embodiment, the inner surfaces 130 and 135, of the surge layers, 128 and 134, are not in liquid communication with the same portions of the garment facing region 47 of the absorbent core 46. The surge layers 128 and 134 may extend laterally across and be in liquid communication with the garment facing region 47 of the absorbent core 46 any width as desired. With regards to the second portions of the inner surfaces, 130 and 135, of the surge layers, 128 and 134, it is to be understood that the second portions of the inner surfaces, 130 and 135, of the surge layers, 128 and 134, need not be in liquid communication with the entire longitudinal length of the longitudinal side edges, 60 and 62, of the absorbent core 46.

Figure 4:
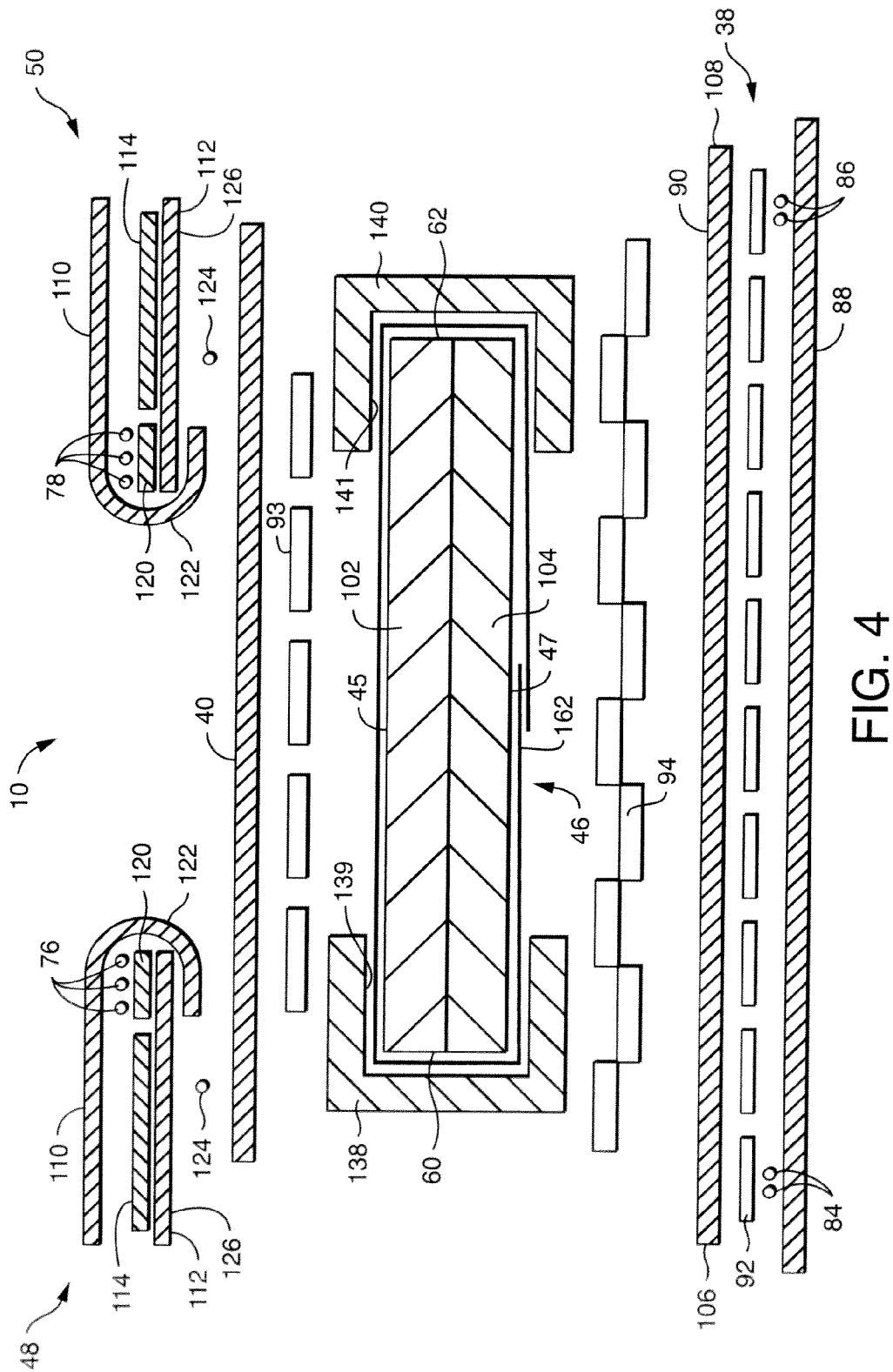
FIG. 4 is a separated cross-section of a second embodiment of the absorbent article of FIG. 1 taken laterally through the crotch region of the absorbent article.
Figure 5:
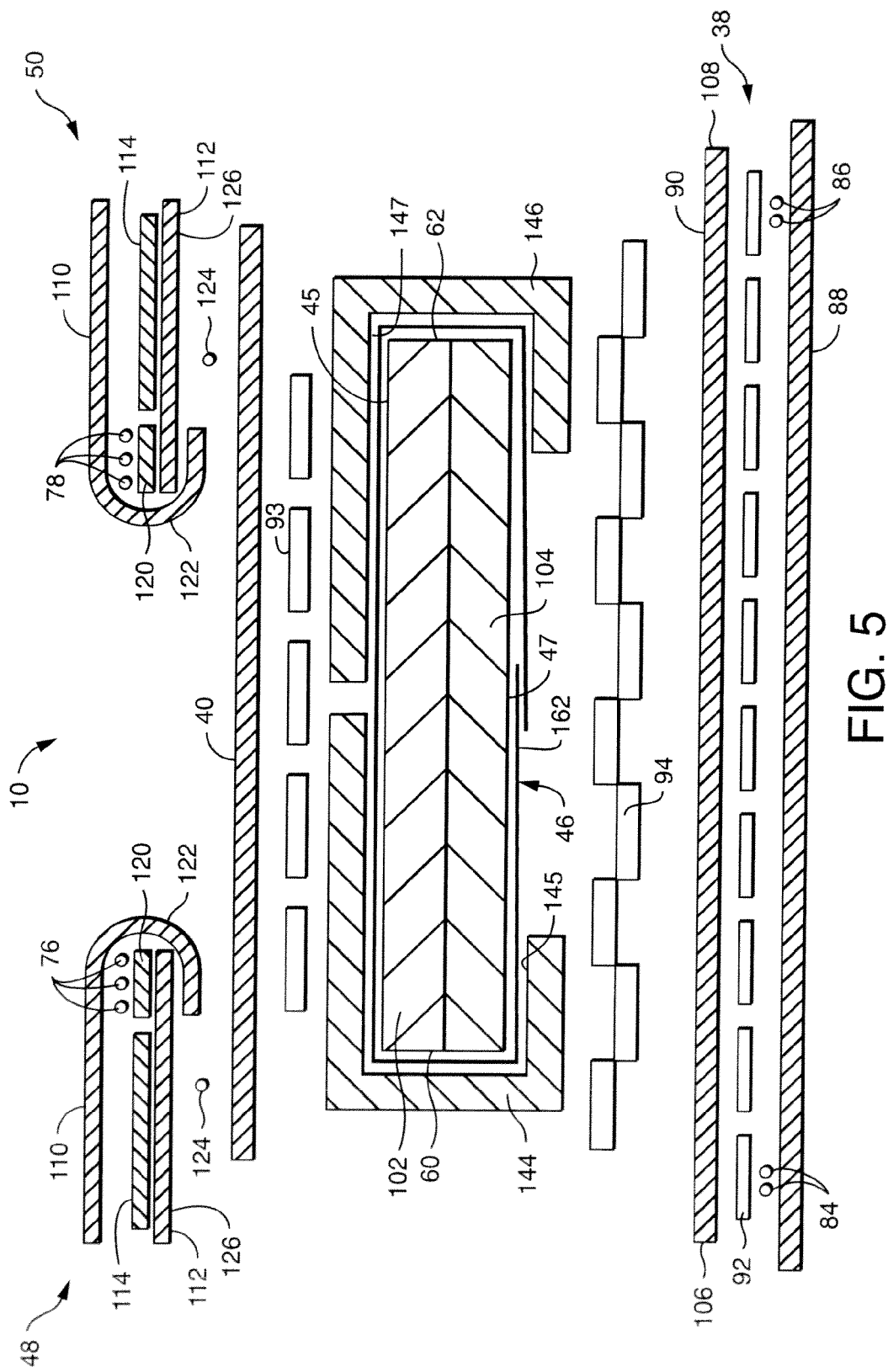
FIG. 5 is a separated cross-section of a third embodiment of the absorbent article of FIG. 1 taken laterally through the crotch region of the absorbent article.

FIG. 4 is an illustration of a separated cross-section of an embodiment of an absorbent article 10 comprising two surge layers 138 and 140. In such an embodiment, a first portion of the inner surface 139 of surge layer 138 and a first portion of the inner surface 141 of surge layer 140 are in liquid communication with first and second portions, respectively, of the garment facing region 47 of the absorbent core 46. Also in such an embodiment, a second portion of the inner surface 139 of surge layer 138 and a second portion of the inner surface 141 of surge layer 140 are in liquid communication with portions of the longitudinal side edges, 60 and 62, respectively, of the absorbent core 46. Additionally, a third portion of the inner surface 139 of surge layer 138 and a third portion of the inner surface 141 of surge layer 140 are in liquid communication with first and second portions, respectively, of the wearer facing region 45 of the absorbent core 46. It is to be understood that in the illustrated embodiment, the inner surfaces 139 and 141 of the surge layers, 138 and 140, are not in liquid communication with the same portions of the garment facing region 47 or the wearer facing region 45 of the absorbent core 46. The surge layers 138 and 140, may extend laterally across the garment facing region 47 of the absorbent core 46 any width as desired. Also, the surge layers 138 and 140, may extend laterally across the wearer facing region 45 of the absorbent core 46 any width as desired. With regards to the second portions of the inner surfaces, 139 and 141, of the surge layers, 138 and 140, it is to be understood that the second portions of the inner surfaces, 139 and 141, of the surge layers, 138 and 140, need not be in liquid communication with the entire longitudinal length of the longitudinal side edges, 60 and 62, of the absorbent core 46. FIG. 5 is an illustration of a separated cross-section of an embodiment of an absorbent article 10 comprising two surge layers 144 and 146. In such an embodiment, a first portion of the inner surface 145 of surge layer 144 and a first portion of the inner surface 147 of surge layer 146 are in liquid communication with first and second portions, respectively, of the garment facing region 47 of the absorbent core 46. Also in such an embodiment, a second portion of the inner surface 145 of surge layer 144 and a second portion of the inner surface 147 of surge layer 146 are in liquid communication with portions of the longitudinal side edges, 60 and 62, of the absorbent core 46. Additionally, a third portion of the inner surface 145 of surge layer 144 and a third portion of the inner surface 147 of surge layer 146 are in liquid communication with first and second portions, respectively, of the wearer facing region 45 of the absorbent core 46. In the illustrated embodiment it will be seen that the third portion of the inner surface 145 of surge layer 144 and the third portion of the inner surface 147 of surge layer 146 are in liquid communication with the wearer facing region 45 of the absorbent core 46 substantially across the lateral width of the wearer facing region 45 of the absorbent core 46. However, it is to be understood that the third portions of the inner surfaces, 145 and 147, of the surge layers, 144 and 146, do not need to be in liquid communication with the wearer facing region 45 of the absorbent core 46 substantially across the lateral width of the wearer facing region 45 of the absorbent core 46. It is also to be understood that one of the third portions of the surge layers, 144 or 146, could be in liquid communication across more of the lateral width of the wearer facing region 45 of the absorbent core 46 than the other third portion of surge layer, 144 or 146. With regards to the second portions of the inner surfaces, 145 and 147, of the surge layers, 144 and 146, it is to be understood that the second portions of the inner surfaces, 145 and 147, of the surge layers, 144 and 146, need not be in liquid communication with the entire longitudinal length of the longitudinal side edges, 60 and 62, of the absorbent core 46.

Figure 6:
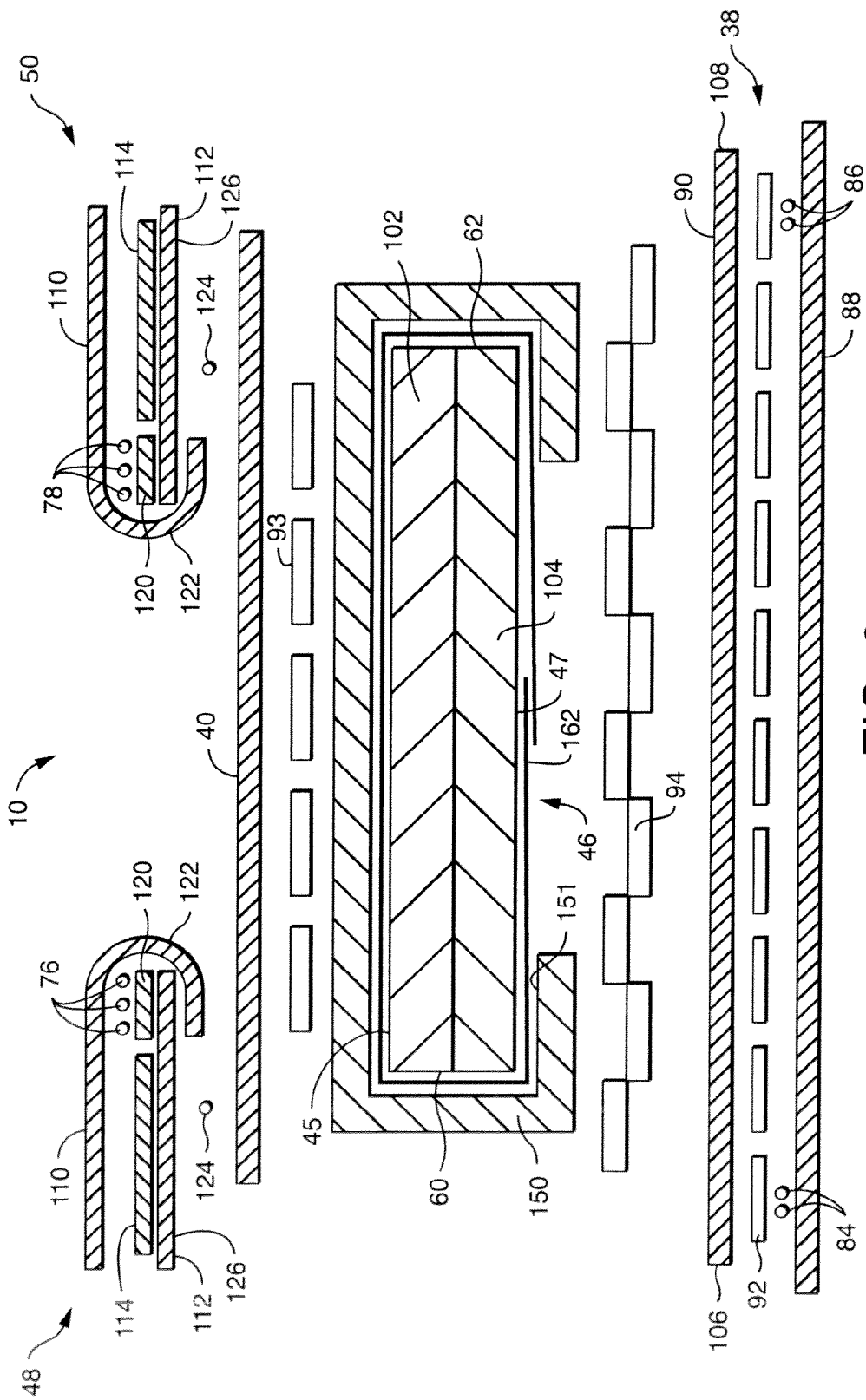
FIG. 6 is a separated cross-section of a fourth embodiment of the absorbent article of FIG. 1 taken laterally through the crotch region of the absorbent article.

FIG. 6 is an illustration of a separated cross-section of an embodiment of an absorbent article 10 comprising a single surge layer 150. In such an embodiment, a first portion of the inner surface 151 of surge layer 150 is in liquid communication with a first portion of the garment facing region 47 which is contiguous with longitudinal side edge 60. A second portion of the inner surface 151 of surge layer 150 is in liquid communication with a second portion of the garment facing region 47 wherein the second portion of the garment facing region 47 is contiguous with longitudinal side edge 62. Additionally in this embodiment, a third portion of the inner surface 151 of surge layer 150 is in liquid communication with longitudinal side edge 60. A fourth portion of the inner surface 151 of surge layer 150 is in liquid communication with longitudinal side edge 62. Further in such an embodiment, the inner surface 151 of surge layer 150 is in liquid communication with the wearer facing region 45 of the absorbent core 46. As shown in the illustrated embodiment, the inner surface 151 of surge layer 150 is in liquid communication with the wearer facing region 45 of the absorbent core 46 across the lateral width of the wearer facing region 45 of the absorbent core 46. With regards to the third and fourth portions of the inner surface 151 of the surge layer 150 in liquid communication with portions of the longitudinal side edges, 60 and 62, respectively, it is to be understood that the third and fourth portions of the inner surface 151 of the surge layer 150 need not be in liquid communication with the entire longitudinal length of the longitudinal side edges, 60 and 62, of the absorbent core 46.

Figure 7:
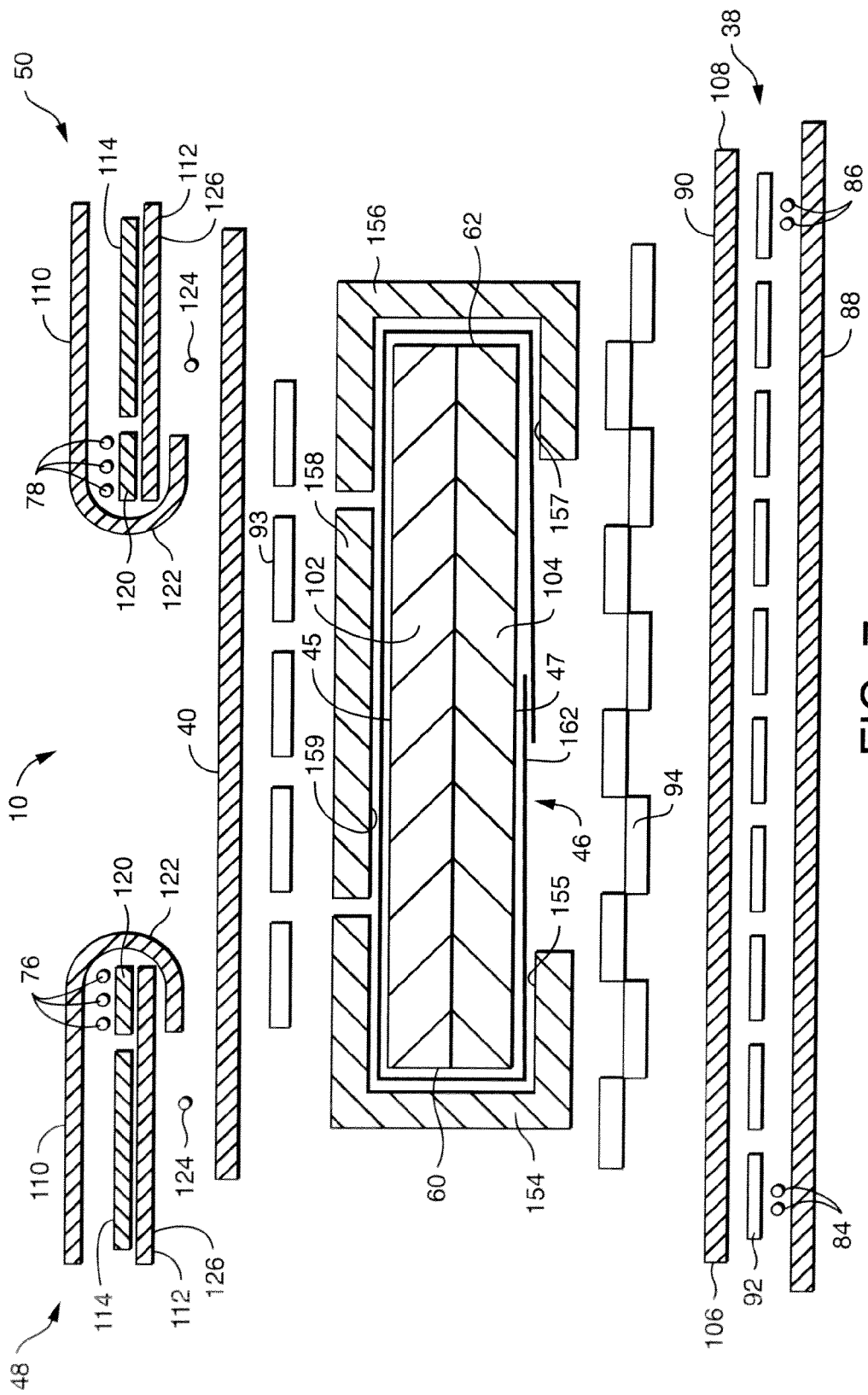
FIG. 7 is a separated cross-section of a fifth embodiment of the absorbent article of FIG. 1 taken laterally through the crotch region of the absorbent article.

FIG. 7 is an illustration of a separated cross-section of an embodiment of an absorbent article 10 comprising three surge layers 154, 156, and 158. In such an embodiment, a first portion of the inner surface 155 of surge layer 154 and a first portion of the inner surface 157 of surge layer 156 are in liquid communication with the first and second portions, respectively, of the garment facing region 47 of the absorbent core 46. Also in such as an embodiment, a second portion of the inner surface 155 of surge layer 154 and a second portion of the inner surface 157 of surge layer 156 are in liquid communication with portions of the longitudinal side edges, 60 and 62, of the absorbent core 46. Additionally, a third portion of the inner surface 155 of surge layer 154 and a third portion of the inner surface 157 of surge layer 156 are in liquid communication with first and second portions, respectively, of the wearer facing region 45 of the absorbent core 46. The inner surface 159 of surge layer 158 is in liquid communication with the wearer facing region 45 of the absorbent core 46. With regards to the second portions of the inner surfaces, 155 and 157, of the surge layers, 154 and 156, it is to be understood that the second portions of the inner surfaces, 155 and 157, of the surge layers, 154 and 156, need not be in liquid communication with the entire longitudinal length of the longitudinal side edges, 60 and 62, of the absorbent core 46. The third surge layer 158 may extend across the lateral width of the wearer facing region 45 as desired. As such, the third surge layer may extend across the lateral with the wearer facing region 45 until it is contiguous with the first and second surge layers, 154 and 156, respectively. Alternatively, the third surge layer 158 may be separate from and not contiguous with the first and second surge layers, 154 and 156, respectively.

Bodyside Liner:

The bodyside liner 40 of the absorbent article 10 overlays the absorbent core 46 and the outer cover 38 and isolates the wearer's skin from liquid waste retained by the absorbent core 46. The bodyside liner 40 may be secured to the absorbent core 46, such as by being bonded thereto by an adhesive 93. The bodyside liner 40 extends beyond the absorbent core 46 to overlay a portion of the inner layer 90 of the outer cover 38 and is secured thereto, such as by being bonded thereto by adhesive 94, to substantially enclose the absorbent core 46 between the outer cover 38 and the bodyside liner 40. The bodyside liner 40 may be slightly narrower than the outer cover 38, but it is also to be understood that the bodyside liner 40 and the outer cover 38 may be of the same dimensions, or the bodyside liner 40 may be sized larger than the outer cover 38, without departing from the scope of this disclosure. It is also contemplated that the bodyside liner 40 may not extend beyond the absorbent core 46 and may not be secured to the outer cover 38 and/or to the absorbent core 46. The bodyside liner 40 is suitably compliant, soft feeling, and non-irritating to the wearer's skin and can be less hydrophilic than the absorbent core 46 to provide a relatively dry surface to the wearer and permit liquid body waste to readily penetrate through its thickness. Alternatively, the bodyside liner 40 can be more hydrophilic or can have essentially the same affinity for moisture as the absorbent core 46 to present a relatively wet surface to the wearer to increase the sensation of being wet. This wet sensation can be useful as a training aid. The hydrophilic/hydrophobic properties can be varied across the length, width and/or depth of the bodyside liner 40 and absorbent core 46 to achieve the desired wetness sensation of leakage performance.

The bodyside liner 40 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and non-woven fabrics can be used for the bodyside liner 40. For example, the bodyside liner 40 can be composed of a meltblown or spun-bond web of polyolefin fibers. Alternatively, the bodyside liner 40 can be a bonded-carded web composed of natural and/or synthetic fibers. The bodyside liner 40 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 40 or it can be selectively applied to particular sections of the bodyside liner 40.

A suitable bodyside liner 40 is constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure.

Also, although the outer cover 38 and bodyside liner 40 of the central absorbent assembly 28 can include elastomeric materials, it is contemplated that the central absorbent assembly 28 may instead be generally inelastic, wherein the outer cover 38, the bodyside liner 40 and the absorbent core 46 are composed of materials which are generally non-elastomeric. In an embodiment, the bodyside liner 40 can be stretchable, and more suitably elastic. In an embodiment, the bodyside liner 40 is suitably stretchable and more suitably elastic in at least the lateral or circumferential direction of the absorbent article 10. In other aspects, the bodyside liner 40 can be stretchable, and more suitably elastic, in both the lateral and the longitudinal directions.

Side Panels:

The front side panels 30 and 32 and the back side panels 34 and 36 of the absorbent article 10 are bonded to the central absorbent assembly 28 in the respective front and back waist regions, 14 and 16, and extend outwardly beyond the side edges, 56 and 58, of the central absorbent assembly 28. In an example, the front side panels, 30 and 32, can be secured to the inner layer 90 of the outer cover 38, such as being bonded thereto by adhesive, by pressure bonding, by thermal bonding or by ultrasonic bonding. These side panels, 30 and 32, may also be secured to the outer layer 88 of the outer cover 38, such as by being bonded thereto by adhesive, by pressure bonding, by thermal bonding, or by ultrasonic bonding. The back side panels, 34 and 36, may be secured to the outer and inner layers, 88 and 90 respectively, of the outer cover 38 at the back waist region 16 of the absorbent article 10 in substantially the same manner as the front side panels, 30 and 32. Alternatively, the front side panels, 30 and 32, and the back side panels, 34 and 36, may be formed integrally with the central absorbent assembly 28, such as by being formed integrally with the outer cover 38, the bodyside liner 40 or other layers of the absorbent article 10.

For improved fit and appearance, the front side panels, 30 and 32, and the back side panels, 34 and 36, suitably have an average length measured parallel to the longitudinal axis of the absorbent article 10 that is about 20 percent or greater, and more suitably about 25 percent or greater, of the overall length of the absorbent article 10, also measured parallel to the longitudinal axis. For example, absorbent articles 10 having an overall length of about 54 centimeters, the front side panels, 30 and 32, and the back side panels, 34 and 36, suitably have an average length of about 10 centimeters or greater, and more suitably have an average length of about 15 centimeters. Each of the front side panels, 30 and 32, and back side panels, 34 and 36, can be constructed of one or more individual, distinct pieces of material. For example, each front side panel, 30 and 32, and back side panel, 34 and 36, can include first and second side panel portions (not shown) joined at a seam (not shown), with at least one of the portions including an elastomeric material. Alternatively, each individual front side panel, 30 and 32, and back side panel, 34 and 36, can be constructed of a single piece of material folded over upon itself along an intermediate fold line (not shown).

The front side panels, 30 and 32, and back side panels, 34 and 36, each have an outer edge 96 spaced laterally from the engagement seam 74, a leg end edge 98 disposed toward the longitudinal center of the absorbent article 10, and a waist end edge 100 disposed toward a longitudinal end of the absorbent article 10. The leg end edge 98 and waist end edge 100 extend from the side edges, 56 and 58, of the central absorbent assembly 28 to the outer edges 96. The leg end edges 98 of the front side panels, 30 and 32, and back side panels, 34 and 36, form part of the side edges, 20 and 22, of the absorbent article 10. The leg end edges 98 of the illustrated absorbent article 10 are suitably curved and/or angled relative to the transverse axis to provide a better fit around the wearer's legs. However, it is understood that only one of the leg end edges 98 can be curved or angled, such as the leg end edge 98 of the back waist region 16, or neither of the leg end edges 98 can be curved or angled, without departing from the scope of this disclosure. The waist end edges 100 are suitably parallel to the transverse axis. The waist end edges 100 of the front side panels, 30 and 32, form part of the front waist edge 24 of the absorbent article 10, and the waist end edges 100 of the back side panels, 34 and 36, form part of the back waist edge 26 of the absorbent article 10.

The front side panels, 30 and 32, and back side panels, 34 and 36, suitably include an elastic material capable of stretching laterally. Suitable elastic materials, as well as one described process for incorporating elastic front side panels, 30 and 32, and back side panels, 34 and 36, into an absorbent article 10 are described in the following U.S. Pat. No. 4,940,464 issued Jul. 10, 1990 to Van Gompel et al., U.S. Pat. No. 5,224,405 issued Jul. 6, 1993 to Pohjola, U.S. Pat. No. 5,104,116 issued Apr. 14, 1992 to Pohjola, and U.S. Pat. No. 5,046,272 issued Sep. 10, 1991 to Vogt et al.; all of which are incorporated herein by reference. As an example, suitable elastic materials include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., and PCT Application WO 01/88245 in the name of Welch et al., all of which are incorporated herein by reference. Other suitable materials are described in U.S. patent application Ser. No. 12/649,508 to Welch et al. and Ser. No. 12/023,447 to Lake et al., all of which are incorporated herein by reference. Alternatively, the front side panels, 30 and 32, and back side panels, 34 and 36, may include other woven or non-woven materials, such as those described above as being suitable for the outer cover 38 or bodyside liner 40, mechanically pre-strained composites, or stretchable but inelastic materials.

Containment Flaps:

Containment flaps, 48 and 50, are secured to the bodyside liner 40 in generally parallel, spaced relation with each other laterally inward of the leg openings, 70 and 72, to provide a barrier against the flow of urine to the leg openings, 70 and 72. The containment flaps, 48 and 50, extend longitudinally from the front waist region 14 of the absorbent article 10, through the crotch region 18 to the back waist region 16 of the absorbent article 10. Each containment flap, 48 and 50, comprises a non-woven layer 110 and a film layer 112 secured to the non-woven layer 110, such as by being bonded thereto by adhesive 114. Flap elastics, 76 and 78, are secured by suitable adhesive 120 between the non-woven layer 110 and the film layer 112, generally at a distal end 122 of the containment flaps, 48 and 50, with the non-woven layer 110 being folded over the flap elastics, 76 and 78, and the film layer 112 at the distal end 122. The containment flaps, 48 and 50, are secured to the bodyside liner 40 by a seam of adhesive 124 to define a proximal end 126 of the containment flaps, 48 and 50.

The flap elastics, 76 and 78, as illustrated, comprise three strands of elastomeric material extending longitudinally along the distal ends 122 of the containment flaps, 48 and 50, in generally parallel, spaced relation with each other. The elastic strands are secured between the non-woven layer 110 and the film layer 112 while in an elastically contractible condition such that contraction of the strands gathers and shortens the distal ends 122 of the containment flaps, 48 and 50. As a result, the elastic strands bias the distal ends 122 of each containment flap, 48 and 50, toward a position spaced from the proximal end 126 of the containment flaps, 48 and 50, so that the containment flaps, 48 and 50, extend away from the bodyside liner 40 in a generally upright orientation of the containment flaps, 48 and 50, especially in the crotch region 18 of the absorbent article 10, when the absorbent article 10 is fitted on the wearer. It is understood, however, that the containment flaps, 48 and 50, may be omitted from the absorbent article 10 without departing from the scope of this disclosure.

Leg Elastics:

Leg elastic members, 84 and 86, are secured between the outer and inner layers, 88 and 90, respectively, of the outer cover 38, such as by being bonded therebetween by a laminate adhesive 92, generally adjacent lateral outer edges, 106 and 108, of the inner layer 90 of the outer cover 38. Alternatively, the leg elastic members, 84 and 86, may be disposed between other layers of the absorbent article 10. A wide variety of elastic materials may be used for the leg elastic members, 84 and 86. Suitable elastic materials include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example with the application of heat, such that the elastic retractive forces are imparted to the substrate.

Flow Control Layer:

A flow control layer (not shown) may be disposed between the inner and outer layers, 102 and 104, respectively, of the absorbent core 46 to retard the rate at which urine received into the absorbent core 46 passes from the inner layer 102 to the outer layer 104. The flow control layer may have a width and length substantially the same as the widths and lengths of the inner and outer layers, 102 and 104, respectively, of the absorbent core 46. However, it is to be understood that the flow control layer may be narrower and/or shorter than the inner and outer layers, 102 and 104, respectively, or wider and/or longer than the inner and outer layers, 102 and 104, respectively without departing from the scope of this disclosure. The flow control layer may be constructed of either an impermeable material or a permeable material, it being understood that the rate at which urine passes from the inner layer 102 of the absorbent core 46 to the outer layer 104 of the absorbent core 46 is generally a function of the permeability of the flow control layer. As an example, a suitable material from which the flow control layer may be constructed is a polypropylene or polyethylene film having apertures formed therein to permit urine to flow therethrough.

The apertures may be sized in the range of about 1 mm to about 10 mm and the aperture density of the film may be less than or equal to about 14 apertures per square inch of the film. The thickness of the film may be less than or equal to about 0.003 inches.

Another suitable material for construction of the flow control layer is a meltblown, hydrophobic non-woven material. The material suitably has a basis weight of about 0.6 ounces per square yard and a thickness of less than or equal to about 1 mm It is also contemplated that the flow control layer may be constructed of other permeable materials without departing from the scope of this disclosure.

As another example, a suitable impermeable material from which the flow control layer may be constructed is a film material, such as a polyethylene or polypropylene film, devoid of apertures to severely retard the flow of urine from the inner layer 102 of the absorbent core 46 to the outer layer 104 of the absorbent core 46. Urine received by the inner layer 102 of the absorbent core 46 is instead directed by the flow control layer to migrate outward (e.g., through the inner layer 102 of the absorbent core 46) toward peripheral edges of the flow control layer and then around the edges thereof to the outer layer 104 of the absorbent core 46. In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a. an absorbent core comprising:
      i. a wearer facing region;
      ii. a garment facing region;
      iii. a first side edge connecting the wearer facing region and the garment facing region;
   b. a surge layer comprising:
      i. a first portion in liquid communication with a first portion of the garment facing region of the absorbent core; and
      ii. a second portion in liquid communication with a portion of the first side edge of the absorbent core;
   wherein the absorbent article further comprises a second surge layer; and
   wherein the second surge layer comprises a first portion in liquid communication with a second portion of the garment facing region of the absorbent core and a second portion in liquid communication with a portion of a second side edge of the absorbent core.

2. The absorbent article of claim 1 wherein the surge layer further comprises a third portion in liquid communication with a first portion of the wearer facing region of the absorbent core.

3. The absorbent article of claim 1 wherein the side edge of the absorbent core is a longitudinal side edge.

4. The absorbent article of claim 1 wherein the side edge of the absorbent core is an end edge.

5. The absorbent article of claim 1 wherein the second surge layer further comprises a third portion in liquid communication with a second portion of the wearer facing region of the absorbent core.

6. The absorbent article of claim 1 wherein the absorbent article further comprises a third surge layer.

7. The absorbent article of claim 6 wherein the third surge layer is in liquid communication with the wearer facing region of the absorbent core.

8. The absorbent article of claim 1 further comprising a core wrap.

9. The absorbent article of claim 1 further comprising a pair of containment flaps.

* * * * *